United States Patent [19]

Heilman et al.

[11] 4,030,509

[45] June 21, 1977

[54] IMPLANTABLE ELECTRODES FOR ACCOMPLISHING VENTRICULAR DEFIBRILLATION AND PACING AND METHOD OF ELECTRODE IMPLANTATION AND UTILIZATION

[75] Inventors: Marlin S. Heilman, Gibsonia; Alois A. Langer, Pittsburgh, both of Pa.; Mieczyslaw Mirowski, Owings Mills; Morton M. Mower, Baltimore, both of Md.; David M. Reilly, Pittsburgh, Pa.

[73] Assignee: Mieczyslaw Mirowski, Owings Mills, Md.

[22] Filed: Sept. 30, 1975

[21] Appl. No.: 620,026

[52] U.S. Cl. .......................... 128/419 D; 128/416; 128/418; 128/419 P
[51] Int. Cl.² .......................................... A61N 1/36
[58] Field of Search ...... 128/404, 416, 418, 419 D, 128/419 P, 419 R

[56] References Cited

UNITED STATES PATENTS

| | | | |
|---|---|---|---|
| 2,985,172 | 5/1961 | Jones | 128/419 D |
| 3,244,174 | 4/1966 | Wesbey et al. | 128/418 |
| 3,348,548 | 10/1967 | Chardack | 128/418 |
| 3,389,703 | 6/1968 | Criswell et al. | 128/418 |
| 3,543,761 | 12/1970 | Bradley | 128/418 |
| 3,572,344 | 3/1971 | Bolduc | 128/418 |
| 3,572,345 | 3/1971 | Auphan | 128/419 D |
| 3,614,954 | 10/1971 | Mirowski et al. | 128/419 D |
| 3,737,579 | 6/1973 | Bolduc | 128/418 |

FOREIGN PATENTS OR APPLICATIONS

| | | | |
|---|---|---|---|
| 2,260,564 | 12/1972 | Germany | 128/419 R |

OTHER PUBLICATIONS

Rosenbaum, "Surgery", vol. 37, No. 5, May, 1955, pp. 712-713.
Schuder et al., "Transactions of the American Society for Artificial Internal Organs", vol. 16, 1970, pp. 207-212.
Medtronics, "Chaddacendocardiac Electrodes", Dec., 1968, pp. 1-20.
Deal et al., "Journal of Thoracic & Cardiovascular Surgery", vol. 55, No. 3, Mar., 1968, pp. 359-360.

*Primary Examiner*—William E. Kamm
*Attorney, Agent, or Firm*—Fleit & Jacobson

[57] ABSTRACT

Disclosed are several embodiments of an electrode system for ventricular defibrillation, and the methods of using and implanting the electrode system. In one embodiment, the electrodes are in a generally base-apex configuration having a split conformal base electrode residing above the base of the ventricles (a transecting plane separating the atria from the ventricles) in the region of the atria and a conformal apex electrode in the form of a rotated conic section residing at the apex of the heart. In another embodiment, defibrillation is accomplished by the apex electrode acting against a catheter electrode situated high in the heart or in the superior vena cava.

The electrodes themselves are in the form of planar metallic mesh elements adapted to lie in contact with body tissue on an active surface, insulated on the opposite surface. In another embodiment, the conductive portions of the respective electrodes are developed from metallic plates, exposed on one surface and insulated on the other. The electrodes may be split, or may entirely surround the base and apex of the heart.

The disclosed electrode system is well adapted for easy implantation during an open heart surgery, or in a separate operation which can be performed in the mediastinal space without intrusion of the pleural space. The electrode system may be implanted for immediate stand-by defibrillation, or may be implanted during open heart surgery, used for post-operative monitoring, pacing and defibrillation, should the need arise, and then subcutaneously implanted for future association with an automatic defibrillating pulse generator. When employed after open heart surgery, the electrode system is preferably equipped with independent atrial and ventricular pacer electrodes.

Also disclosed are techniques for fixing the electrode system to the surrounding body tissue, and electrode leads which may be removed after the implanted electrodes have served their desired function, without disturbing the electrodes themselves.

31 Claims, 14 Drawing Figures

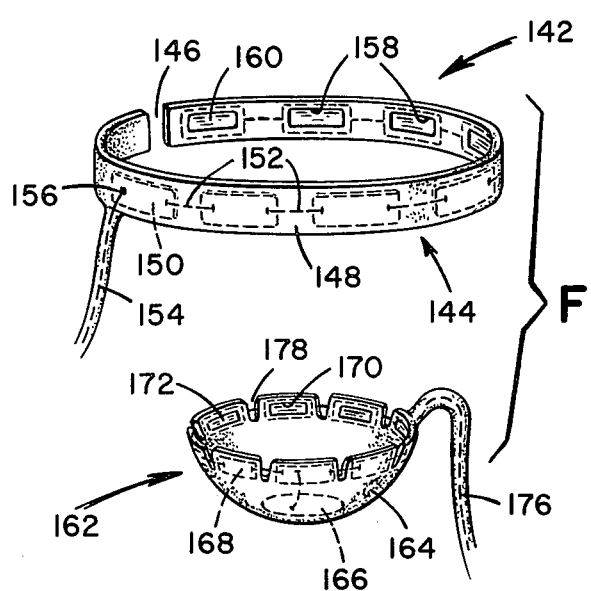
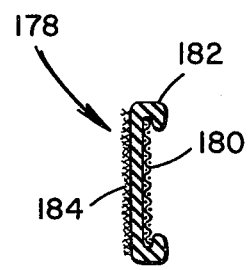
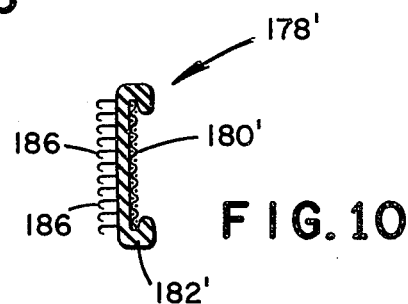
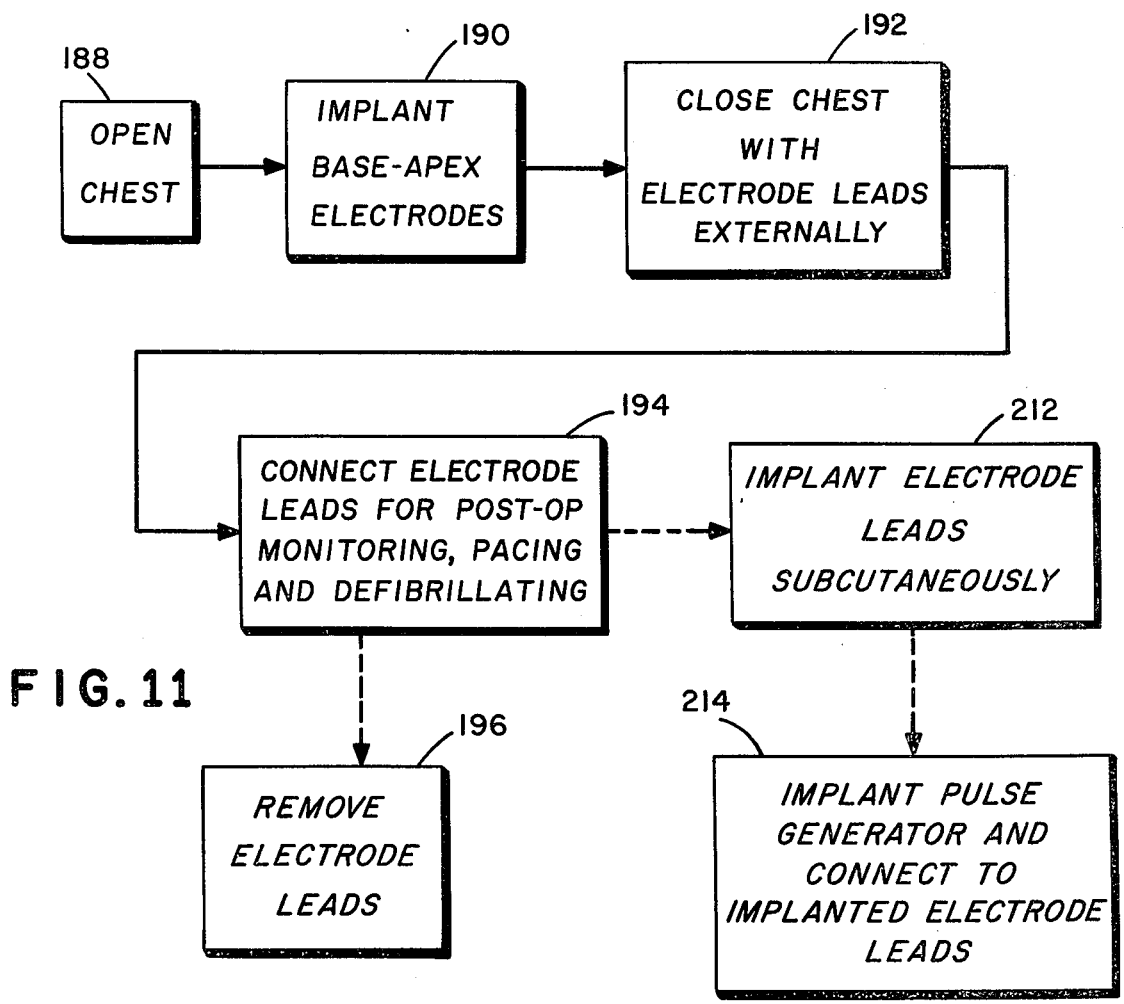

IMPLANTABLE ELECTRODES FOR ACCOMPLISHING VENTRICULAR DEFIBRILLATION AND PACING AND METHOD OF ELECTRODE IMPLANTATION AND UTILIZATION

BACKGROUND OF THE INVENTION

It has been known for years that ventricular fibrillation, a fatal arrhythmia, can be reversed by passing high energy electric current through the fibrillating myocardium. In a hospital coronary care environment, defibrillation is generally accomplished by means of external chest paddles placed on the patient's thorax, with current being diffused through the chest. While defibrillation is in this manner generally successful, only a portion of the applied current affects the myocardium, and hence substantial amounts of electrical energy must be introduced to the already suffering body of the patient.

In open heart surgery, internal paddles are commonly applied directly to the surface of the heart. Typically, such endothoracic paddles are circular in configuration, of a conductive metal such as stainless steel, and are approximately 10 cm. in diameter. In use, these paddles are generally applied to opposite surfaces of the ventricular myocardium in a sandwich-type fashion.

A modern approach to defibrillation considers the use of a single intravascular catheter electrode system having two discrete electrodes (or electrode sets) on the catheter. In catheter defibrillation, the electrical current travels from one electrode to the other, setting up an electrical field which affects a critical mass of the myocardium. By so depolarizing this critical mass, the heart is brought back to normal cardiac rhythm.

In humans, external paddle defibrillation is known to require from 100 to 400 watt-seconds of energy, while endothoracic paddle defibrillation employed during heart surgery generally requires the application of energy somewhere on the order of 10 to 50 watt-seconds. The approach of catheter defibrillation has reduced the energy requirements to somewhere between 5 and 35 watt-seconds.

The utilization of an implantable automatic defibrillator implies an elective installation of the necessary electrodes, for if fibrillation is in progress, there is no time for the installation of internal electrodes. Being an elective procedure, where the election to implant electrodes is based upon the statistical probability of the occurrence of ventricular fibrillation, it is clear that the acceptability of a given electrode system will be a function of how easily the electrodes can be installed, assuming, of course, acceptable performance. If a catheter electrode system is used, the installation consists of the relatively simple placement pervenously of a bielectrode catheter the tip of which goes into the apex of the right ventricle. Yet there is a need for defibrillating electrodes which more efficiently discharge energy into the heart.

There are an extremely large number of coronary bypass operations done yearly (approximatley 50,000) on patients with coronary artery disease. For the most part, these patients are at a high risk of ventricular fibrillation and other potentially fatal arrhythmias, both during the post-operative phase and on a long term basis. Immediately after the coronary artery has been bypassed, but before the chest is closed, there is an opportunity to install electrodes for accomplishing ventricular defibrillation. At this time, a set of electrodes, if available, could be laid into position on the heart surface.

The heart is normally covered with a pericardial membrane or sac. During coronary bypass surgery, the pericardium is incised and laid open to gain access to the coronary arteries, enabling the implantation of electrodes between the pericardium and the epicardial surface of the heart. Or, if the pericardium were to be partially destroyed during surgery, the chest would still be open to enable the placement of suitable electrodes at another location. For example, one or both of the electrodes could be sutured to the outside of the pericardium or other remaining structures. Accordingly, there is a need for defibrillating, or more generally, cardioverting electrodes which are suitable for implantation on or about the heart during open heart surgery, such as coronary bypass surgery.

Furthermore, being an elective procedure, it is important that the implantation of cardioverting electrodes be made possible at minimum risk to the patient. With the exception of the catheter, there are no known cardioverting electrodes which can be implanted without entering the pleural space, necessitating a general anesthetic and respiration assistance. There is accordingly a great need for cardioverting electrodes which may be implanted through the means of a relatively simple surgical procedure.

While defibrillator technology has advanced significantly since its inception, it may still be thought of as in its infancy. This is especially true with respect to the automatic implantable defibrillator. The present invention adds one further dimension to medical electronics, and in particular to the field of low energy reliable automatic implantable defibrillation.

SUMMARY OF THE INVENTION

The present invention is generally related to the field of electrical defibrillation, and more specifically to electrode configurations for implantable ventricular defibrillators, and methods for their implantation.

In one embodiment, two conformal electrodes are applied to the external intrapericardial or extrapericardial surface of the heart in a configuration that may be termed base-apex. One electrode associates with the apex of the heart generally in the form of a cup, and the other electrode contacts the base of the heart in a generally circumferential fashion. In a preferred embodiment, the base electrode is split, and is positioned slightly above the base and in association with the atria. Each electrode is insulated on its surface facing away from the heart, so that substantially all current flowing between the electrodes passes through the ventricular myocardium. The electrically conductive surfaces are preferably in the form of wire mesh, but may also comprise metallic plate-like segments held in an insulating base material. Independent pacing tips are preferably associated with both the base and apex electrodes. In another embodiment, the apex electrode operates against an intravascular catheter base electrode.

In describing the base and apex electrodes in the following paragraphs, the term electrode is most often used to designate not only the conductive element, but the combination of the conductive element and the insulating material. Accordingly, to conform to the shape of the heart, the apex conductive element preferably takes a substantially frustoconical shape, at least throughout a portion of its surface, while the insulating package preferably defines what can be viewed as a relatively deep rotated parabola.

With the electrode configurations described above, substantially all of the electrical energy applied to and flowing across the electrodes reaches the critical regions of the heart to accomplish defibrillation. The associated electronic package can therefore be made smaller, with lower energy requirements, and the life of the unit can be significantly extended. More importantly, by means of the inventive electrode system, defibrillation is accomplished with relatively little trauma to the cardiac tissue.

In its preferred form, the inventive electrode system comprises base and apex electrodes of a fine mesh (on the order of 150 mesh), with each electrode preferably having on the order of at least 12 square centimeters of surface area. The mesh is preferably of platinum, but may be of stainless steel or a platinum alloy, and is preferably embedded into an insulating form. The apex elect.ode is constructed from an elongated flat strip of mesh, is held in a conical shape through the means of the insulating material, and is split, so as to enable flexion of the lower regions of the ventricles.

The base electrode is also preferably split, comprising a large and a small section totalling at least about 12 square centimeters in area. With the base electrode so split, there is no constriction of the pulmonary artery. Nor is atrial movement significantly restricted.

It is anticipated that the base electrode extend at least 70° around the circumference of the atria, up to approximately 240°. Preferably, the base electrode extends between 90° and 180° around the atria. The apex electrode is able to extend substantially entirely around the apex of the heart. The base electrode is designed to reside about the atria, above the auriculo-ventricular groove so as to avoid constriction of the coronary arteries, while the apex electrode is designed to reside in the lower one-third of the axial length of the heart. With such a configuration, it is possible to cardiovert either the atria or the ventricles. Furthermore, both the base and apex electrodes are designed to include pacing tips extending approximately 2 to 3 millimeters from the main electrode surface, for both positioning and pacing functions.

Because of the relative simplicity of the inventive electrode system, it is anticipated that the inventive electrodes could be implanted during open heart surgery and left in place with external leads through the skin of the patient for post-operative monitoring, pacing, or defibrillation, if necessary. Then, after the brief post-operative period, the leads could be extracted, leaving the electrodes themselves implanted. Alternatively, the proximal ends of the electrode leads could be implanted subcutaneously, with the electrodes remaining in place. Later, should it be deemed advisable for the patient to wear an automatic defibrillator, a small incision could be made, a pulse generator implanted, and the pulse generator connected to the already implanted electrode leads.

The present invention also contemplates electrode implantation during a surgical procedure not involving intrusion into the pleural space. This method of implantation consists first of making a surface incision which exposes the pericardium. The xiphoid process may or may not be excised. Then, using retraction, the medial lateral surface of the pericardial heart covering is brought into view, and a pericardial incision extending approximately 2 inches in length is made. The two sections of the split base electrode are then together positioned in a set of ring type forceps and inserted through the pericardial incision. The base electrode positioning may be aided by image amplified fluoroscopy and/or the use of the above-described sensing and pacing electrode protruding from the surface of the electrode structure. To minimize wandering of the base electrode within the pericardial space, various position fixing mechanisms could be employed. The base electrode is positioned with the two sections on opposite sides of the pulmonary artery to avoid constriction. The base electrode sections are preferably placee over the atria, so that potential constriction of the coronary arteries is also avoided. The most energy efficient position of the base electrode is believed to be circumferentially high on the ventricles immediately below the coronary sulcus, or auriculo-ventricular groove.

The apex electrode may then be placed through the pericardial incision into a position which is conformal to the apex of the left ventricle. As long as the lead is strain relieved, this electrode has little tendency to move away from its correct position, and therefore hooks and the like should not be necessary.

It is therefore one object of the present invention to provide electrodes for accomplishing low energy cardioversion or defibrillation, and hence for enhancing the practicality of an automatic implantable defibrillator.

Another object of the present invention is to provide a defibrillator which minimizes the possibility of heart damage by increasing the efficiency of energy utilization during defibrillation.

A further object of the present invention is to provide direct cardiac defibrillation electrodes which are useful for implantation in any situation where the heart is exposed.

Still another object of the present invention is to provide a defibrillating electrode system which can be deployed around the heart with minimum surgery.

An additional object of the present invention is to provide an electrode system for defibrillation which enjoys the advantages of catherization and efficiency of electrical discharge.

A further object of the present invention is to provide an electrode system with which the application of electrical energy is restricted to and generally evenly distributed in the heart during defibrillation.

A related object of the present invention is to provide an electrode system which avoids undesirable concentration and waste of electrical energy.

Another object of the present invention is to provide an electrode system which allows expansion and contraction of the heart without undue restriction of or abrasion to body tissues.

Yet a further object of the present invention is to provide a flexible electrode system which includes electrically conductive elements, means for facilitating implantation and means for maintaining the desired electrode position.

Yet another object of the present invention is to provide an electrode system designed so that during implantation, the electrodes take the contour of the heart, naturally or temporarily through fixation, thereby facilitating the necessary operative procedure.

A further object of the present invention is to provide a cardioverting electrode system having a large surface area, and yet being flexible so as to permit cardiac activity without trauma.

Another object of the present invention is to provide a cardioverting electrode system which avoids constriction of the coronary and pulmonary arteries.

A further object of the present invention is to provide a cardioverting electrode system which may be implanted without intrusion into the pleural space.

Another object of the present invention is to provide a cardioverting electrode system equipped with a pacing tip.

A further object of the present invention is to provide a cardioverting electrode which may be implanted during open heart surgery, and used for post-operative monitoring and defibrillating, and then later attached to a pulse generator.

Another object of the present invention is to provide a defibrillating electrode system wherein the electrodes are capable of defibrillating both the atria and the ventricles.

A further object of the present invention is to provide an electrode system capable of implantation in the pericardial space.

Another object of the present invention is to provide an electrode system which may readily be implanted during open heart surgery and left in the body after a post-operative period.

A related object of the present invention is to provide an implantable electrode system whose electrical leads may be removed without disturbing the implanted electrodes.

Another object of the present invention is to provide a method for implanting defibrillating electrodes without entry of the pleural space.

Still a further object of the present invention is to provide an electrode system having silver tinsel wound ribbon leads.

These and other objects of the present invention, as well as many of the attendant advantages thereof, will become more readily apparent when reference is made to the following description, taken in conjunction with the accompanying drawings.

BRIEF DESCRIPTION OF THE DRAWINGS

FIG. 8 is a perspective view illustrating a second embodiment of the inventive base-apex electrode system;

FIG. 9 is a cross section through a base electrode showing one manner of attaching the electrode to the body tissue;

FIG. 10 is a cross section similar to FIG. 9, but showing another mechanism for attaching the base electrode to the body tissue;

FIG. 11 ia a flow diagram illustrating two operative procedures utilizing the inventive base-apex electrode system;

DETAILED DESCRIPTION OF THE DRAWINGS

Figure 1:
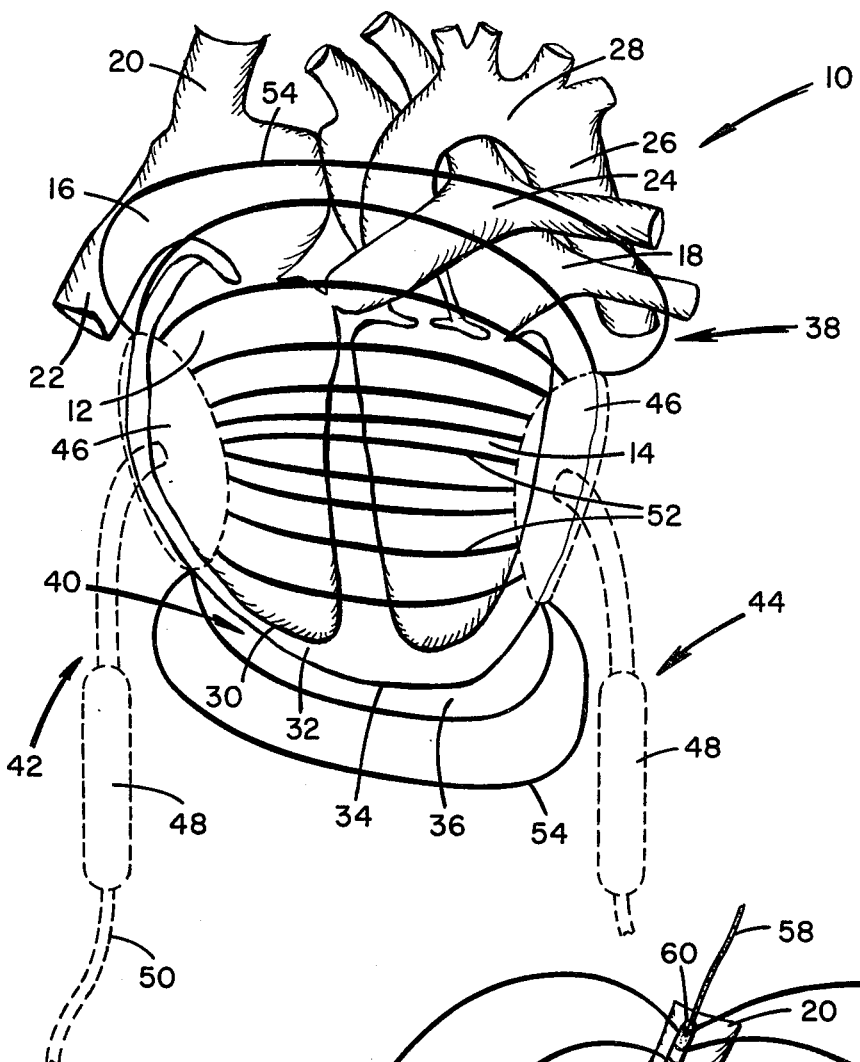
FIG. 1 is a schematic anterior view of a heart showing the placement of conventional defibrillating paddles.

With reference first to FIG. 1, the general configuration of a heart will be described. The heart is shown generally at 10, with the right ventricle illustrated at 12 and the left ventricle at 14. The right and left atria are shown, respectively, at 16 and 18. The superior vena cava is illustrated at 20, and supplies blood to the right atrium 16, as does the interior vena cava 22. The pulmonary artery is shown at 24, with the aorta and aortic arch illustrated at 26 and 28, respectively. The endocardium is indicated at 30, with 32 representing the myocardium and 34 the epicardium of the heart 10. The pericardial space is indicated at 36, though the pericardium is not illustrated. The base of the heart is indicated generally at 38, and as the term is used herein, represents the region of the heart wherein the atria and the ventricles meet. The apex of the heart can be seen at 40.

A pair of defibrillating paddles 42 and 44 are shown in contact with the right and left ventricles, respectively, and sandwich the heart 10 therebetween. Each paddle comprises a generally circular conductive member 46, an insulated handle 48 adapted to be held by the operator, and electrical leads 50. When electrical energy is applied across paddles 42 and 44 an electrical field is set up, denoted by field lines 52 and 54. The more concentrated field lines are shown at 52, while the more diverse and scattered lines can be seen at 54. Generally speaking, the electrical field developed by the known internal defibrillating paddles is fairly well concentrated, and quite effective for purposes of defibrillation.

Figure 2:
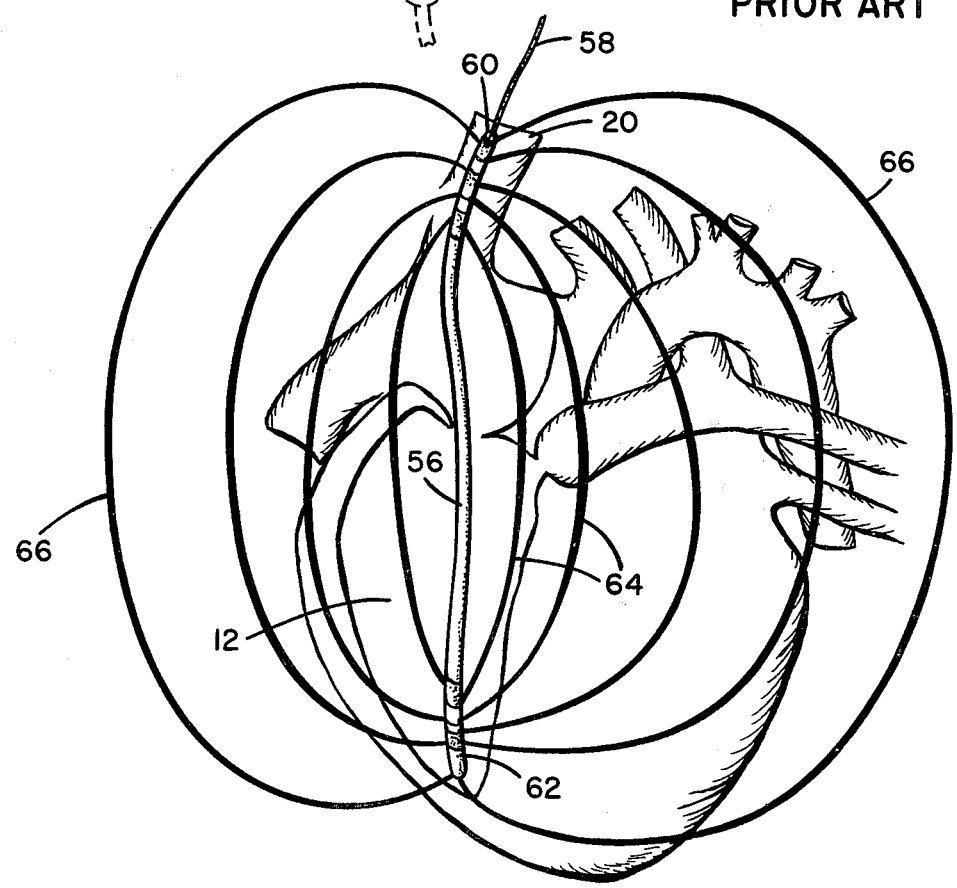
FIG. 2 is a view similar to FIG. 1, but illustrating the placement and discharge pattern for a known defibrillating catheter.

With reference now to FIG. 2, another known defibrillating electrode will be described. This electrode is in the form of a catheter 56. Electrical leads 58 provide energy to the catheter 56, which includes a proximal electrode 60 and a distal electrode tip 62, each shown as a set of conductive rings. The distal electrode 62 is adapted to reside in the apex of the right ventricle 12, while the proximal electrode 60 is designed to lie, for example, in the superior vena cava 20. When electrical energy is applied between electrodes 60 and 62, an electrical field is developed, represented by field lines 64 and 66. As can be seen, the field lines 64 are concentrated mainly in the region of the right ventricle 12, with some of the energy being shunted through the blood. The more remote field lines 66 travel through the respective left and right ventricles, and aid in converting the fibrillating ventricles. Though catheter defibrillation as illustrated in FIG. 2 has been found to be quite effective, it appears that blood shunting necessitates the application of relatively high amounts of energy for effective defibrillation.

Figure 3:
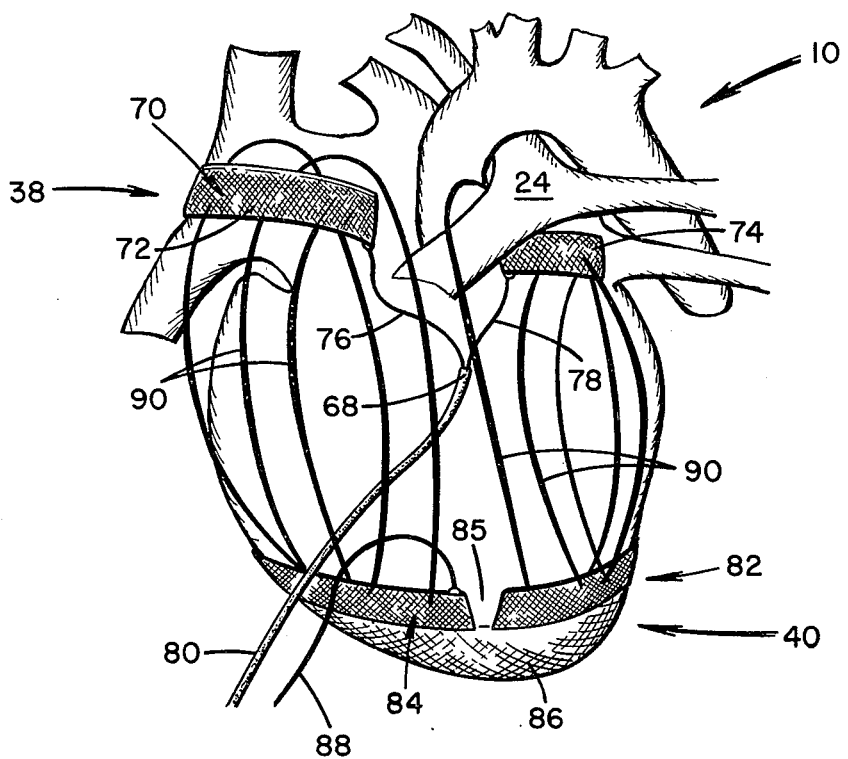
FIG. 3 is a schematic anterior view of a heart equipped with a conformal base-apex electrode system constructed in accordance with the teachings of the present invention.

With reference now to FIG. 3, the inventive base-apex electrode system will be described. This inventive system comprises a base electrode which is shown generally at 70, and an apex electrode shown generally at 82. In this embodiment, both the base electrode 70 and the apex electrode 82 are split, with the base electrode 70 comprising a right section 72 and a left section 74. As is illustrated, the right section 72 is the largest, and is adapted to lie over the anterior and lateral surface of the right atrium. The smaller left section 74 is designed to lie over the anterior and lateral surface of the left atrium. It should be noted that in this embodiment, the pulmonary artery 24 is avoided so as not to constrict the same. Separate electrical leads 76 and 78 associate, respectively, with base electrode sections 72 and 74, and are united at junction 68 to form a "Y" with a main electrode lead 80. Though not illustrated, it should be obvious that all electrode leads 76, 78 and 80 are insulated from body tissue. Furthermore, the right and left base electrodes 72 and 74 are insulated from body tissue on the respective sides thereof facing away from the heart 10. The electrodes 72 and 74 are conductive on the surfaces facing the heart.

The apex electrode 82 comprises a band 84 of electrically conductive material which substantially surrounds the entire circumference of the apex 40. The band 84 is split at 85 so as to enable adaptation to various apical forms. The surface of the apex electrode 82 facing away from the heart is covered by an insulating material 86 which cups the entire apex of the heart. The surface of the apex electrode 82 facing the heart, like that of the base electrode 70, is conductive. Electrical energy is delivered to the apex electrode 82 through the means of lead 88 which, as is illustrated, extends upwardly from the apex of the heart. In this manner, the apex electrode may be positioned entirely within the mediastinal space, without invasion of the pleural space.

When electrical energy is applied between the respective leads 80 and 88, a field is developed as shown by field lines 90 in FIG. 3. The field lines 90 are substantially well concentrated in the heart itself, passing between base and apex electrodes 70 and 82 with a minimum amount of electrical energy being wasted. As a result of this concentration in electrical energy, it is possible to defibrillate an ailing heart with less electrical energy than has heretofore been possible.

Figure 4:
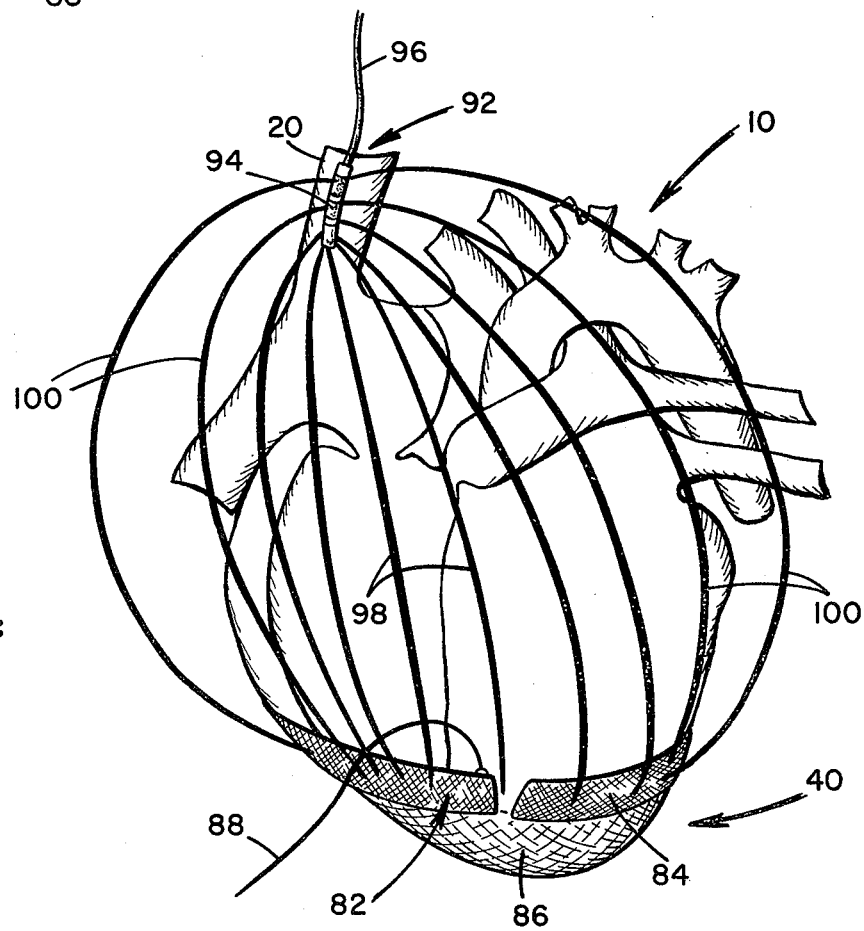
FIG. 4 is a view similar to FIG. 3, but showing a second embodiment of the present invention having a conformal apex electrode operating against a catheter electrode in the superior vena cava.

With reference now to FIG. 4, a second embodiment of the inventive electrode system will be described. In this embodiment, the apex 40 is equipped with an apex electrode 82 identical to that described above when reference was made to FIG. 3. The apex electrode 82 comprises a conformal conducting belt 84 insulated at its exterior surface by means of an insulating layer 86 defining a cup about the apex of the heart. Apex electrode 82, in this embodiment, acts against a catheter electrode shown generally at 92.

Electrode 92 is in the form of a small intravascular catheter adapted to reside in the superior vena cava 20. The conductive elements of the catheter 92 are in the form of bands 94, fed with electrical energy through the means of lead 96. When electrical energy is applied through leads 88 and 96, and hence between electrodes 82 and 92, an electrical field is developed across the heart 10, which is represented by field lines 98 and 100. The more central field lines 98 pass through the central regions of the heart, while the more remote field lines 100 encompass the generally external surfaces of the ventricles. In this embodiment, more electrical energy flows through the myocardium than in the prior art configuration illustrated in FIG. 2. By replacing the prior art right ventricular distal electrode with a generally circumferential external apex electrode, the field lines must of necessity pass through the myocardium when flowing from one electrode to the other.

Figure 5:
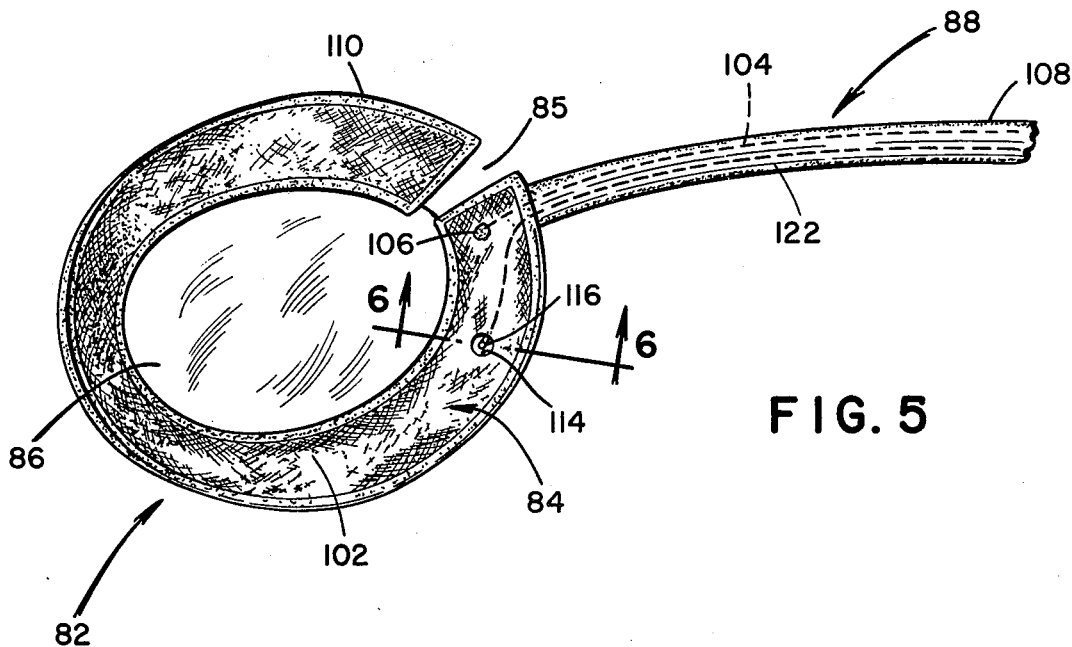
FIG. 5 is a perspective interior view of the apex electrode illustrated in FIG. 3.
Figure 6:
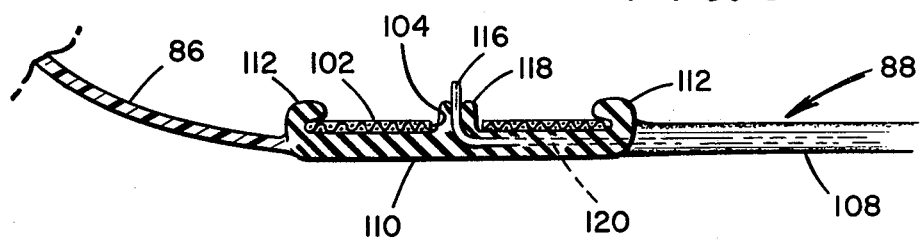
FIG. 6 is a cross section of the apex electrode taken at plane 6—6 of FIG. 5.
Figure 7:
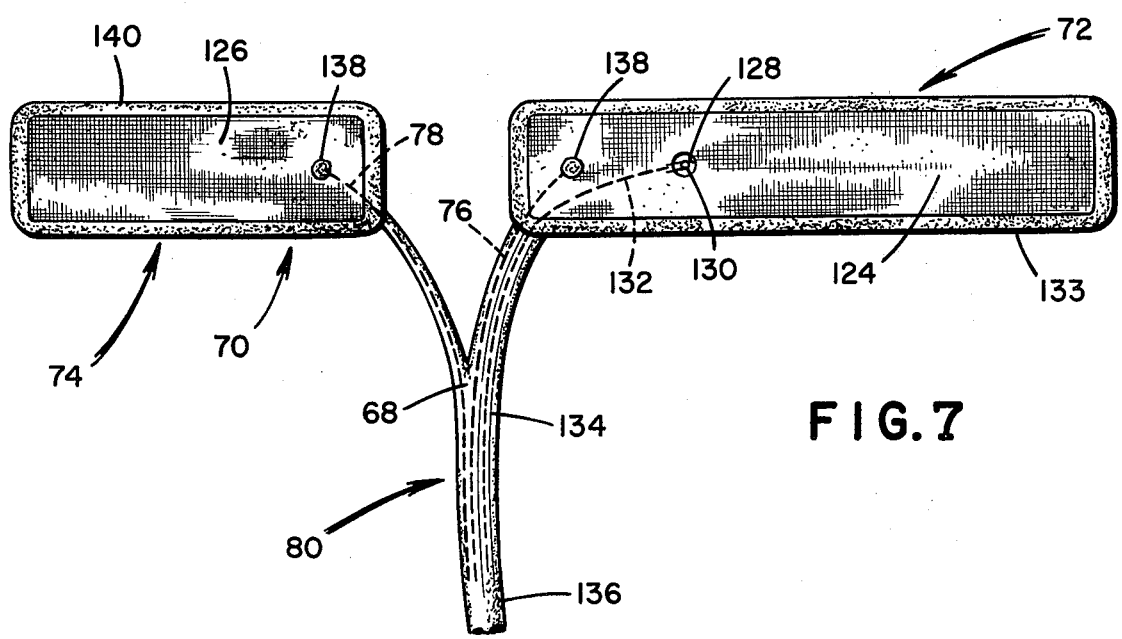
FIG. 7 illustrates the interior surface of the base electrode shown in FIG. 3.

FIGS. 5 through 7 illustrate the details of the preferred embodiment of the inventive base and apex electrodes. FIG. 5 is a perspective view of the surface of the apex electrode 82 which faces the heart. FIG. 7 is a similar view showing the conductive surface of the base electrode 70. The conductive material forming the band 84 of the apex electrode 82 is shown at 102 and comprises a fine metallic mesh. The mesh may be of any highly conductive material, such as platinum, silver or platinum alloy, and as presently contemplated, will have approximately 150 elements per linear inch. Each element of the mesh 102 is contemplated to be on the order of 1 to 3 mils in diameter. An electrical lead 104, the construction of which will be explained in detail below, is welded to the mesh 102 at 106, and lies within a flexible insulating casing 108 to form an electrical lead package shown generally at 88.

As seen best in FIG. 6, the external side of the apex electrode 82 is covered by an insulating material 110, as of silicone rubber, for example, surrounding the wire mesh 102 at its edges, as seen at 112. By totally imbedding the edges of mesh 102 in the flexible and non-abrasive insulating material 110, the possibility of tissue damage is minimized. The insulating material 110 extends into the central region of the apex electrode 82 to form the cup 86 seen best in FIG. 3.

A small hole 114 is cut into the mesh 102, so as to maintain electrical insulation between conductive mesh 102 and a small, rigid conductive tip 116. The tip 116 extends through opening 114, about the surface of mesh 102, and in the direction of the heart. Tip 116 is coated by the insulating material 110 in the region of the opening 114, as shown at 118. The proximal end of tip 116 is embedded within the insulating material 110, is in electrical communication with a lead at 120, and extends through the insulating casing 108. The electrical lead of the tip 116 is insulated from the lead 104 as shown in FIG. 5 at 122. As will be described in greater detail below, tip 116 is a pacing tip, and is adapted to pierce the epicardium in the region of apex 40.

The base electrode illustrated in FIG. 7 is constructed similar to the apex electrode 82 described above when reference was made to FIGS. 5 and 6. The right section 72 of the base electrode 70 includes a wire mesh 124. A wire mesh 126 forms the conductive element of the left base electrode section 74. An opening 128 is cut into the wire mesh 124 in the right section 72, and a pacing tip 130, insulated from mesh 124 by means of insulating material 133 extends toward the surface of the heart. Tip 130 is connected to an electrical lead 132 embedded in the insulating material 133, and is continuous with an insulated lead wire 134 housed within the boundaries of insulating casing 136. Insulating casing 136 also houses electrical leads 76 and 78, which are connected to the respective wire meshes of the right and left base electrodes at welding points 138. The metallic mesh 126 of the left base electrode section 74 is insulated at its exterior surface by a layer of silicone rubber insulation 140 similar to insulating material 133.

In the embodiment of the inventive base-apex electrode system illustrated in FIGS. 3, 5 and 7, it is contemplated that the apex electrode lie somewhere in the lower one-third of the heart. It is also contemplated that the base electrode extend somewhere between 70° and 240° around the circumference of the heart in the region of the atria. The respective pacing tips 116 and 130 are preferably of a generally rigid wire extending 2 to 3 mm from the surface of the metallic meshes. The pacing tips are designed for connection to pacing electronics, insulated from defibrillating electronics which associate with the large area metallic mesh electrodes. A typical size for the large right section of the base electrode would be on the order of 1×7 cm., while the smaller left section would be on the order of 1×4 cm. The apex electrode, on the other hand, could be on the order of 1×12 cm.

With reference now to FIG. 8, a second embodiment of the inventive base-apex electrode system will be described. The base electrode is shown generally at 142, and is in the form of a unitary band 144 split as at 146 so as not to constrict the atria. The band 144 is defined by an insulating strip 148 into which is embedded, or otherwise sandwiched, a plurality of metallic plates 150. Each of the plates 150 is connected to its neighboring plate through the means of electrical conductors 152, and power is delivered to the base electrode 142 through an electrical lead 154, welded to one of the plates 150 as shown at 156. The exterior surface of band 144 is entirely insulated by the insulating material 148, but the interior surface, that which is designed to face the heart, includes a plurality of openings 158 cut into the band of insulating material 148. The interior sides of the plates 150, shown at 160, are shaped to extend through the respective openings 158, and are adapted to lie in contact with the heart, if within the pericardial space, or in contact with the pericardium itself.

The apex electrode is shown in FIG. 8 at 162. The electrode 162 is in the form of a cup, defined by insulating material 164, and is designed to cradle the apex of the heart. A metallic cup 166 lies at the apex of the insulating material 164, and a plurality of plates 168, shaped as a section of a cone, are positioned higher in apex electrode 162. The exterior of the insulating material 164 is continuous, and the interior is provided with a plurality of openings 170 through which the projecting surface 172 of the respective plates 168 extend. The cup 166 and plates 168 are electrically connected together through the means of electrical leads 174, in turn associated with an insulated power lead 176. The apex electrode 162 further includes a plurality of slits 178 so as to allow flexion of the plates 168 when the ventricles contract and expand.

As noted above, it may be appropriate to provide a mechanism for ensuring that the base electrode remains fixed when first implanted. The apex electrode, on the other hand, would probably not require mechanical fixation, but a fixing mechanism could be provided if desired. FIGS. 9 and 10 illustrate two embodiments of mechanisms for fixing the base electrode to the body tissue.

In FIG. 9, the number 178 represents a cross section through a base electrode constructed in accordance with the first embodiment of the present invention. The electrode 178 includes a substantially planar wire mesh electrode 180, and a body of insulating material 182 backing and surrounding the edges of mesh 180. A loosely woven fabric 184 is positioned on the surface of the electrode 178 facing away from the heart. When first implanted, it is contemplated that the apex electrode 178 be maintained in position by means of stylets for a brief period of time (a matter of days). During this time period, the body tissue will naturally grow into the loosely woven fabric 184 to fix the position of the electrode. Then, the stylets would be removed.

In FIG. 10, another embodiment of the fixation mechanism is illustrated. This mechanism provides more immediate fixation of the base electrode, so that placement is ensured without the use of stylets. This embodiment of the base electrode is shown generally at 178', wherein the electrode includes a conductive wire mesh 180' embedded in an insulating material 182'. Mounted on the insulating material 182' at the side thereof facing away from the heart are a plurality of hook-like members 186. When the base electrode 178' is positioned on the epicardium within the pericardial space, the hooks 186 attach themselves to the interior surface of the pericardium, thereby ensuring proper fixation of the electrode 178'.

With reference now to FIG. 11, two operative procedures for utilizing the inventive conformal base-apex electrode system will be described. The flow diagram in FIG. 11 is based upon a first step involving open heart surgery, such as a coronary bypass operation. In performing a coronary bypass, the chest of the patient is opened as indicated in block 188. At the completion of the coronary bypass, after the customary saphenous vein graft, the patient is ready for the implantation of the inventive defibrillating electrodes. Accordingly, the second step in this operative procedure is indicated at 190, and includes the implantation of a base-apex electrode set. With the chest open, and the epicardium exposed, the implantation of base and apex electrodes in the pericardial space is a relatively simple procedure.

After the base and apex electrodes are implanted, the respective electrode leads are positioned external to the surface of the skin, and the chest is closed with the leads so exposed. This step is indicated in FIG. 11 at 192. Then, as is common after open heart surgery, sensing and monitoring equipment are connected to the patient. With the inventive base-apex electrode system, the surgeon has available to him external sensing electrodes in the form of atrial and ventricular pacing tips, as well as base and apex defibrillating electrodes, not before available. Accordingly, monitoring equipment can be connected to the leads of the respective pacing tips of the base and apex electrodes, and so too can demand pacing electronics be connected to these leads. At the same time, the respective base and apex defibrillating electrodes can be connected to either an automatic or a manually actuated defibrillator. This step is indicated at 194. With the operative procedure as described above, the patient is protected from ventricular fibrillation and other arrhythmias which frequently occur during the post-operative period extending typically 3 to 6 days after surgery.

After the post-operative period of 3 to 6 days, two procedures are available to the surgeon. The first is analogous to the common practice of removing a conductive pacing electrode previously sewn to the surface of the heart by pulling the same through the skin. This procedure is illustrated at 196 in FIG. 11, and involves removing the externalized portion of the defibrillating and pacing leads by applying tension to these leads. In this regard, the attention of the reader is directed to FIG. 12, wherein special removable leads are illustrated. Here, a major electrical lead is shown generally at 198, branching off into a Y configuration into separate leads 200 and 202. At the most distal ends of leads 200 and 202 are pins 204 and 206, respectively. These pins 204 and 206 are adapted to mate with female receptacles 208 and 210 which are in electrical communication with right and left base electrode sections 72 and 74.

As an alternative procedure following the remaining branch in FIG. 11, the most proximal ends of the electrode leads can be subcutaneously implanted after the post-operative period. This procedure is indicated at block 212. By maintaining the leads in a subcutaneous condition, they are available for subsequent use should the need ever arise for the application of an automatic implantable defibrillator. In this manner, the necessity for first having to implant defibrillating electrodes is eliminated. Should the patient develop symptoms which would indicate the advisability of implanting an automatic defibrillator, then a surface incision could be made, exposing the subcutaneous leads, and a pulse generator could be implanted and connected to these leads. This step is indicated in FIG. 11 at 214.

Figure 12:
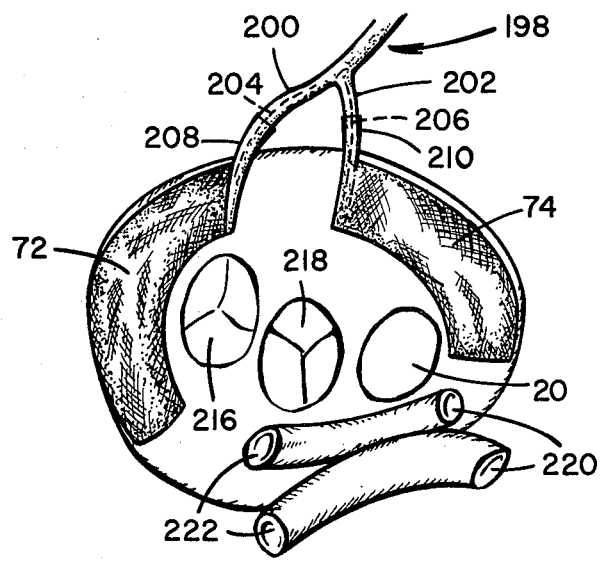
FIG. 12 is a superior view of a heart showing the placement of a split base electrode such as that illustrated in FIG. 3.

The distal ends of the electrical leads 200 and 202 illustrated in FIG. 12 are equipped with tension-release plugs. The same type of plugs can be utilized in enhancing the sterility factor when reserving subcutaneous leads for standby use. In this regard, tension-release plugs could be provided on the respective leads just below the surface of the skin. Then, after the end of the post-operative period, the most proximal portions of the respective leads could be extracted without disturbing the condition of the implanted electrodes, and while leaving electrical leads just below the skin surface for future use.

The foregoing description of electrode implantation was limited to open heart surgery. Yet, with the inventive base-apex electrode system, an operation specific to electrode implantation is still relatively simple, considering that there involves the placement of electrodes on the surface of a heart. This procedure involves first making a subxiphoid incision, and then using retraction to expose the medial lateral surface of the pericardial heart covering. Then, a pericardial incision extending approximately 2 inches in length is made, and the base electrode is positioned in a set of ring type forceps and inserted through the pericardial incision. The base electrode would then be positioned at the base of the heart, and either held in place by one of the fixing mechanisms illustrated in FIGS. 9 and 10, or by applying a stainless steel stylet wire of approximately 0.018 inches in diameter for a period of a few days. Experience has shown that within 1 to 2 days, the body will fix the electrode position by means of a serofibrinous exudate. The stylet would be removed when the electrodes are fibrosed into position.

As noted above, the preferred placement of the split base electrode system is over the atria, to avoid potential constriction of the coronary arteries. It is believed that the most energy efficient position of the base electrode is circumferentially high in the ventricles, immediately below the auriculo-ventricular groove. The apex electrode may then be inserted through the pericardial incision and into a position conformal to the apex of the left ventrical. As long as the apical lead is strain relieved, this electrode has little tendency to move away from its proper position. With reference again to FIG. 12, it can be seen that the split base electrode enables the atria to expand and contract without stress.

Figure 13:
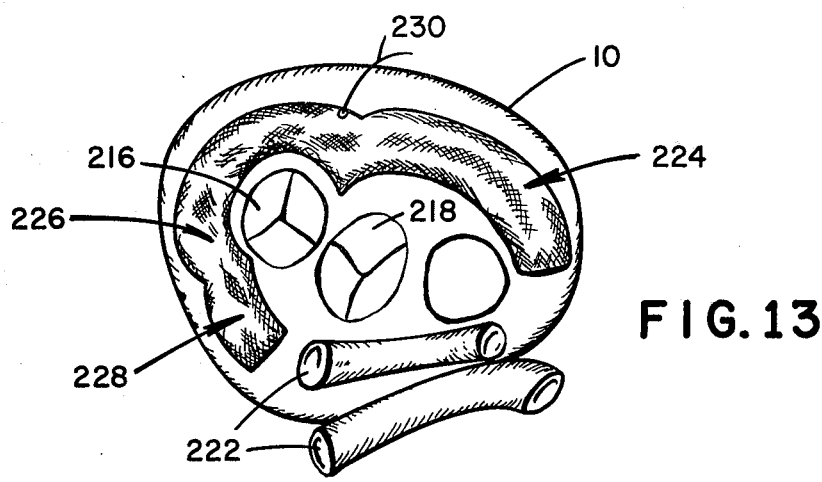
FIG. 13 is a drawing similar to FIG. 12, but illustrating a further embodiment of the base electrode.

Another embodiment of the present invention is illustrated in FIG. 13, which enables the same free movement of the atria, but without a split base electrode. In FIGS. 12 and 13, the pulmonary valve is shown at 216 and the aortic valve at 218. The superior vena cava appears at 20, the right pulmonary veins at 220, and the left pulmonary veins at 222. As will be recalled, and as illustrated in FIG. 3, the split base electrode avoids constriction of the pulmonary artery 24. Similar relief can be accomplished by means of a multi-radial electrode such as that illustrated in FIG. 13.

The base electrode illustrated in FIG. 13 comprises three sections of discrete radii. The first section is indicated generally at 224, and resides on the atria of the heart 10 in the region of the aortic valve 218 and the superior vena cava 20. The second section is shown at 226, and is a section of lesser radius. Section 226 is tailored to conform to the region of the pulmonary artery just above valve 216 and the surrounding cardiac structure. The third section is shown generally at 228 and is again of larger radius, lying at the lateral side of the heart behind the pulmonary artery, and terminating near the left pulmonary veins 222. An electrically conductive lead 230 associates with the base electrode and provides power thereto.

Figure 14:
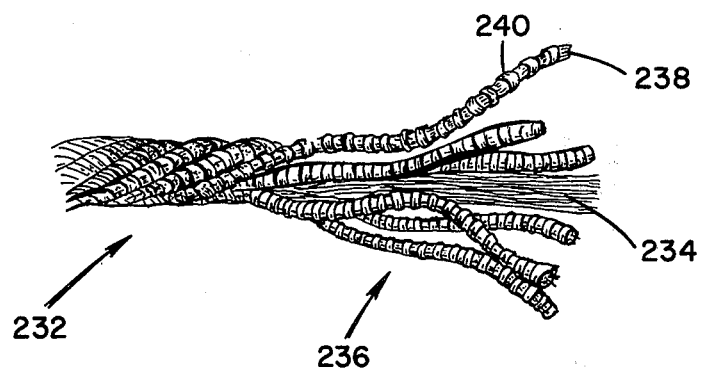
FIG. 14 is a perspective view of an electrical lead constructed in accordance with the teachings of the present invention.

With reference now to FIG. 14, there will be described an electrically conductive lead especially suited for use with implantable defibrillating electrodes. The inventive stranded wire is shown generally at 232 and is of 7-strand construction. The central strand is shown at 234, and comprises a polyester yarn. About core 234 are wound six conductive strands 236. Each strand 236 in turn comprises a core 238 of polyester yarn and wound silver ribbon 240. The silver ribbon 240 is on the order of 13 × 1 mils.

This lead construction as described above is particularly suitable for internal implantation, and is capable of efficiently conducting the high energies utilized in delivering defibrillating shocks to a heart. The wound wire configuration is capable of withstanding virtually indefinite flexions without damage due to the substantial length of silver ribbon relative to the overall length of the lead itself. Furthermore, the silver ribbon is capable of efficiently delivering the high energy generally required when defibrillating a heart.

Above, specific embodiments of the present invention have been described. It should be appreciated, however, that these embodiments were described for purposes of illustration only, without any intention of limiting the scope of the present invention. Rather, it is the intention that the present invention be limited not by the above but only as is defined in the appended claims.

What is claimed is:

1. The combination of an implantable cardioverting electrode and pacing electrode, the combination comprising: conductive base electrode means for associating with the base of the heart; conductive apex electrode means of substantially frustoconical shape throughout at least a portion thereof, for lying adjacent but exterior to the apex of the heart and conforming to the contours thereof; and an auxiliary electrode insulated from both said base and said apex electrodes and extending from the surface of one of said base or said apex electrodes in the direction of the heart, said auxiliary electrode serving to deliver pacing energy to the heart.

2. An electrode system for cardiovering a malfunctioning heart, the electrode system comprising: first conductive electrode means for associating with a heart in the region of its base; second conductive electrode means for associating with the heart in the region of its apex, said second electrode means having first and second conductive surfaces; insulation means for insulating the first conductive surface of said second electrode means; and first and second electrode leads in electrical contact with the respective first and second electrode means, for applying cardioverting electrical energy between said first and second electrode means for discharge through said heart; the second conductive surface of said second electrode means adapted to lie in contact with the heart, and being in a substantially frustoconical shape throughout at least a portion thereof; and the insulation means adapted to face away from the heart, and being in a substantially rotated parabola shape.

3. The electrode system recited in claim 2, wherein said first conductive electrode means comprises first and second discrete sections, sized and shaped so that said first and second sections are adapted to reside on opposite sides of the pulmonary artery.

4. The electrode system recited in claim 2, and further comprising an auxiliary electrode on one of said first and second conductive electrode means insulated therefrom and adapted to contact cardiac tissue; and a third electrode lead associated with said auxiliary electrode for transmitting electrical energy thereto and therefrom.

5. The electrode system recited in claim 2, wherein said first and second conductive electrode means comprise conductive surfaces of metallic mesh for contacting the tissue of the heart.

6. The electrode system recited in claim 2, wherein said first and second conductive electrode means comprise conductive surfaces of metallic plates for contacting the tissiue of the heart.

7. The electrode system recited in claim 2, wherein said first electrode means comprises first and second discrete sections, wherein said first electrode lead has a first component connected to said first section and a second component connected to said second section, and further comprising electrode lead means for joining together said first and second components to form a Y junction.

8. The electrode system recited in claim 2, and further comprising mechanical connector means on at least one of said first or second conductive electrode means for connecting the same to body tissue in the region of the heart.

9. The electrode system recited in claim 2, wherein said first conductive electrode means when relaxed, has a first section of a first radius and a second section of a second and smaller radius, said second section adapted to lie about the pulmonary artery of the heart.

10. The electrode system recited in claim 2, wherein said first conductive electrode means is a catheter electrode adapted to lie high in the heart or in the superior vena cava.

11. The electrode system recited in claim 2, wherein said first and second conductive electrode means are flexible.

12. The electrode system recited in claim 2, wherein said first electrode means is in the shape of a band having a width dimension and a length dimension substantially larger than said width dimension, said band adapted to lie in a circumferential position on the surface of the atrii.

13. The electrode system recited in claim 2, wherein at least one of said first or second conductive electrode means is flexible.

14. An electrode for use in a system for cardioverting a malfunctioning heart, the electrode comprising: conductive means having first and second conductive surfaces; insulation means for insulating the first conductive surface; an electrode lead in electrical connection with said conductive means, for applying cardioverting electrical energy to said conductive means for discharge through a heart; said second conductive surface adapted to lie in contact with the heart, and being of a substantially frustoconical shape throughout at least a portion thereof; and said insulation means adapted to face away from the heart, and being of a substantially rotated parabola shape.

15. The electrode recited in claim 14, wherein said conductive means is defined by a metallic mesh.

16. The electrode recited in claim 14, wherein said conductive means is defined by metallic plates.

17. The electrode recited in claim 14, wherein said conductive means and said insulation means are flexible.

18. The electrode recited in claim 14, and further comprising: an auxiliary electrode insulated from said conductive means and adapted to contact cardiac tissue; and a further electrode lead connected to said auxiliary electrode for transmitting electrical energy thereto and therefrom.

19. The electrode recited in claim 14, wherein said conductive means and said insulating means are split in at least one portion thereof to permit expansion and contraction with the heart.

20. The electrode recited in claim 14, and further comprising: mechanical connector means for connecting the electrode to body tissue in the region of the heart.

21. A method of implanting and utilizing an electrode system for cardioverting a malfunctioning heart, the method comprising the steps of: opening the chest of a patient; positioning a first electrode in the region of the base of the heart; positioning a second permanent conformal electrode around the exterior surface of the apex of the heart; drawing electrical leads from said first and second electrodes outside the body of the patient; closing the chest of said patient with the proximal ends of said electrical leads lying outside the skin of the patient; connecting said electrical leads to post-operative defibrillating electronics; subsequently incising the patient after said post-operative period; implanting a cardioverting pulse generator; connecting the pulse generator to the proximal ends of said electrical leads and closing the incision with said electrical leads and said pulse generator beneath the skin of said patient.

22. The method recited in claim 21, and further comprising the step of: subcutaneously implanting said electrical leads after said post-operative period.

23. The method recited in claim 21, and further comprising the step of: removing the proximal ends of said electrical leads, leaving only the subcutaneous portions of said leads for subsequent association with said pulse generator.

24. The method recited in claim 21, wherein at leat one of said first and second electrodes includes an auxiliary electrode in the surface thereof but insulated therefrom and wherein said electrical leads include an electrical lead associating with said auxiliary electrode; and further comprising the step of connecting monitoring and/or pacing instrumentation to the electrical lead of said auxiliary electrode during said post-operative period.

25. The method recited in claim 21, wherein at least a portion of said electrical leads are removed after said post-operative period without assocation with said pulse generator.

26. A method for implanting cardioverting electrodes, the method consisting of the steps of: forming a first cardioverting electrode adapted to associate with the base of the heart; forming a second substantially frustoconical cardioverting electrode conforming to the natural shape of the apex of the heart; positioning said first electrode in association with the heart in the region of the base thereof; inserting said second electrode through an incision in the pericardium; and positioning said second electrode around the apex of the heart in the pericardial space.

27. The method recited in claim 26, wherein the approach to the pericardial space is through a sub-xiphoid incision with exposure of and incision through the medial lateral surface of the pericardium.

28. The method recited in claim 27, wherein the first electrode conforms to the apex of the heart and the second electrode conforms to and is positioned on the antero-lateral surface of the artria immediately above the atrio-ventricular notch.

29. The method recited in claim 28, wherein at least the first electrode includes a removable wire stylet for aiding in positioning the electrode.

30. A method for implanting permanent cardioverting electrodes in a patient whose heart may require cardioversion, the method comprising the steps of: implanting a first permanent cardiac electrode in the vicinity of the base of the heart; incising the patient to expose the heart; implanting a second permanent conformal electrode about and in contact with the periphery of the apex of the heart; implanting a pulse generator capable of delivering cardioverting pulses to the heart through the first and second electrodes; connecting said first and second electrodes to said pulse generator; and closing the incision made in the patient.

31. The method recited in claim 30, wherein said second permanent conformal electrode is implanted in the pericardial space.

* * * * *